United States Patent
Cole et al.

(10) Patent No.: US 11,980,862 B2
(45) Date of Patent: May 14, 2024

(54) REACTOR AND METHOD FOR REACTING A GAS AND LIQUID REACTANTS

(71) Applicant: Novomer, Inc., Rochester, NY (US)

(72) Inventors: Branden Cole, Caledonia, NY (US); Jeff Uhrig, Media, PA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 18/274,024

(22) PCT Filed: Jan. 19, 2022

(86) PCT No.: PCT/US2022/012914
§ 371 (c)(1),
(2) Date: Jul. 25, 2023

(87) PCT Pub. No.: WO2022/164692
PCT Pub. Date: Aug. 4, 2022

(65) Prior Publication Data
US 2024/0042408 A1    Feb. 8, 2024

Related U.S. Application Data

(60) Provisional application No. 63/143,348, filed on Jan. 29, 2021.

(51) Int. Cl.
| | |
|---|---|
| *C07C 67/36* | (2006.01) |
| *B01J 4/00* | (2006.01) |
| *B01J 8/02* | (2006.01) |
| *B01J 8/06* | (2006.01) |
| *B01J 10/00* | (2006.01) |
| *C07C 67/37* | (2006.01) |

(52) U.S. Cl.
CPC ............ *B01J 10/002* (2013.01); *B01J 4/004* (2013.01); *B01J 8/025* (2013.01); *B01J 8/0278* (2013.01); *B01J 8/065* (2013.01); *C07C 67/36* (2013.01); *C07C 67/37* (2013.01); *B01J 2208/00911* (2013.01); *B01J 2219/00038* (2013.01); *B01J 2219/0004* (2013.01)

(58) Field of Classification Search
CPC . B01J 10/002; B01J 4/004; B01J 8/025; B01J 8/0278; B01J 8/065; B01J 2208/00911; B01J 2219/00038; B01J 2219/0004; C07C 67/36; C07C 67/37
See application file for complete search history.

(56) References Cited

U.S. PATENT DOCUMENTS

| | | |
|---|---|---|
| 6,852,865 B2 | 2/2005 | Coates et al. |
| 9,327,280 B2 | 5/2016 | Lee et al. |
| 10,597,294 B2 | 3/2020 | Sookraj |
| 2004/0068085 A1 | 4/2004 | Belfadhel et al. |
| 2005/0014977 A1 | 1/2005 | Drent et al. |
| 2007/0213524 A1 | 9/2007 | Coates et al. |
| 2019/0030520 A1 | 1/2019 | Lee |

FOREIGN PATENT DOCUMENTS

| | | | |
|---|---|---|---|
| CN | 109692628 A | | 4/2019 |
| EP | 1157081 B2 | | 1/2005 |
| JP | 2013536801 | * | 1/2014 |
| WO | 2020033267 A1 | | 2/2020 |
| WO | 2020050738 A1 | | 3/2020 |
| WO | 2020177753 A1 | | 9/2020 |
| WO | 2021025918 A2 | | 3/2021 |

OTHER PUBLICATIONS

JP2013536801 tanslated 6 pages (Year: 2013).*
International Search Report and Written Opinion in co-pending Application No. PCTUS2022012914 dated Apr. 11, 2022 (10 pages).
International Preliminary Report on Patentability in co-pending Application No. PCT/US2022/012914 dated Apr. 21, 2023 (16 pages).

* cited by examiner

*Primary Examiner* — Yevgeny Valenrod
*Assistant Examiner* — Blaine G Doletski
(74) *Attorney, Agent, or Firm* — Young Basile Hanlon & MacFarlane, P.C.

(57) ABSTRACT

A hybrid vertical plug flow reactor is comprised of a bottom inlet and a top outlet having vertical tubular member disposed there between, wherein the bottom inlet has separate gas reactant inlet and separate liquid reactant inlet whereby the gas reactant is mixed with the liquid reactant and the outlet has an extraction port, the extraction port extending sufficiently to withdraw the liquid product from the reactor and maintain a gaseous head space within the tubular member of the reactor. The hybrid vertical bubble plug flow reactor is useful to react a gas reactant and liquid reactant that are reacted at a molar ratio of gas reactant/liquid reactant that is in excess of a stoichiometric requirement of gas reactant so that the gas reactant forms bubbles and the reactants react in the presence of a catalyst to form a reaction product.

20 Claims, 1 Drawing Sheet

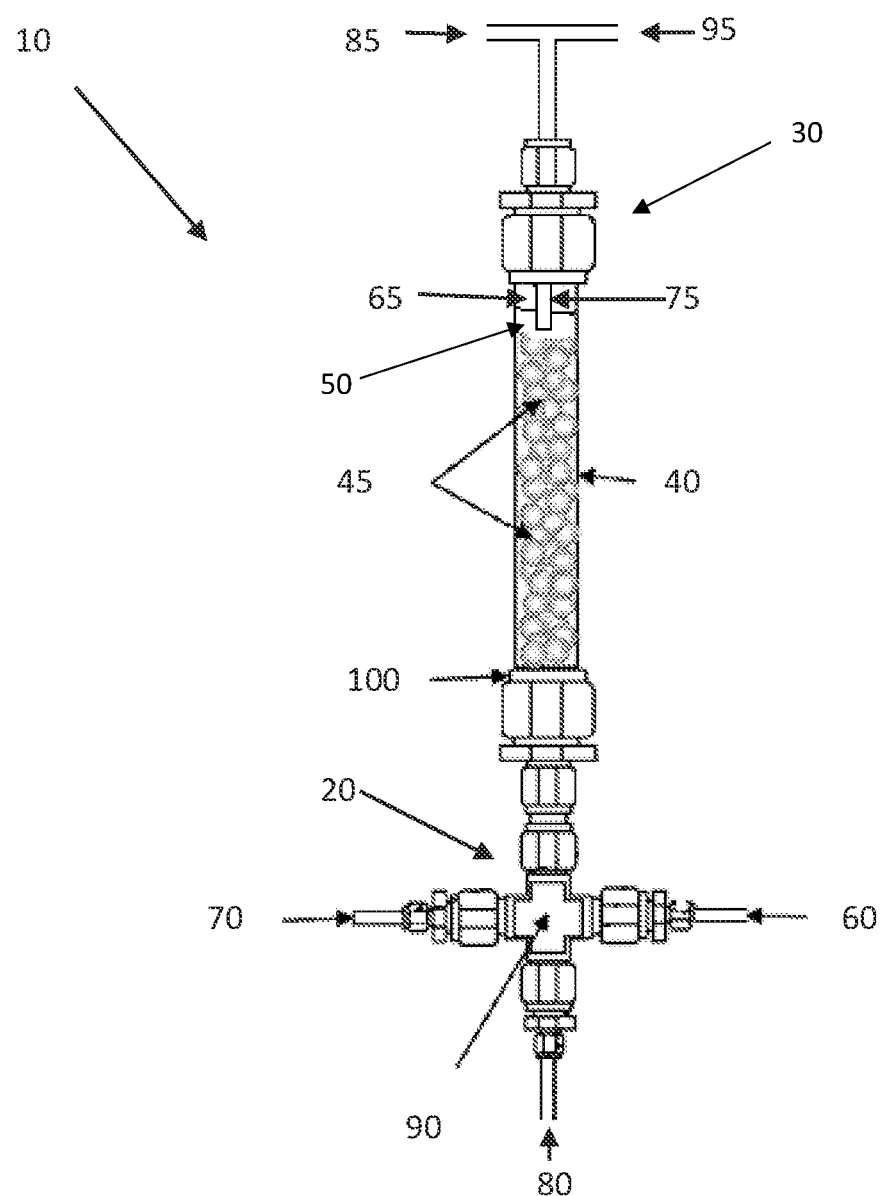

REACTOR AND METHOD FOR REACTING A GAS AND LIQUID REACTANTS

CROSS-REFERENCE TO RELATED APPLICATIONS

This application is a National Stage Filing under 35 USC 371 of the PCT Application No. PCT/US2022/012914 filed Jan. 19, 2022, published Aug. 4, 2022, as WO 2022/164692, which claims priority from U.S. Provisional Application No. 63/143,348 filed Jan. 29, 2021, both of which are incorporated herein by reference in their entirety for all purposes.

FIELD

The invention relates to improved methods for reacting a gas reactant with a liquid reactant. In particular, the invention relates to reacting a gas and liquid in the presence of a catalyst such as the carbonylation of ethylene oxide with carbon monoxide to form beta propiolactone (BPL).

BACKGROUND

The catalyzed reactions of a gas with liquid reactant have typically been performed in stirred batch or continuously stirred reactors maintaining an overpressure of the reactant gas and continuous injection of the gas reactant into the liquid. Batch reactors tend to efficiently use the catalyst (i.e., have a high turnover number "TON" of the catalyst), but suffer from high capital costs for given throughput and down time between batches. In some instances, the stirring of the batch reaction may be accomplished by bubbling the gas reactant through the liquid reactant (i.e., bubble reactor).

Continuously stirred reactors may continuously produce product, but suffer from inefficient use of the catalyst and require continuous separation, recycling and replenishment of the catalyst. Such operations may involve complex methods and techniques such as separation membranes that may foul and result in inconsistent operation or product.

Plug flow reactors have not generally been used for these reactions because typically they involve long coils of tubes to realize sufficient residence time and sufficient heat transfer area. Because these reactions typically require an over feed of the gas reactant, beyond the solubility limit in the liquid/solvent, there often is accumulation of the gas reactant in the high points of the piping resulting in variable liquid hold up/residence time in the reactor as well as inconsistent reaction conditions through the reactor.

Accordingly, it would be desirable to provide a method of reacting a gas and liquid reactant that avoids one or more of the problems of the prior art such as one of those mentioned above.

SUMMARY

Applicant has discovered that a hybrid vertical bubble plug flow reactor ("reactor") herein may be used to react and gas reactant and liquid reactant allowing for well controlled reaction conditions, effective and efficient use of the catalyst (e.g., high TON), while avoiding problems associated with batch bubble reactors, continuous stirred tank reactors and typical plug flow reactors.

The first aspect of the invention is a method of reacting a gas reactant and liquid reactant comprising; (i) introducing the gas reactant and liquid reactant into a hybrid vertical bubble plug flow reactor, having a bottom inlet and a top outlet connected by a tubular member, separately at the bottom inlet, wherein the gas reactant and liquid reactant are mixed and introduced at a rate resulting in a ratio of gas reactant/liquid reactant that is in excess of a stoichiometric amount and the gas reactant forms bubbles within the liquid reactant, (ii) allowing the gas and liquid reactants to react and form a reaction product as they flow upwards through the hybrid vertical bubble plug flow reactor in the presence of a catalyst, and (iii) removing the reaction product at the top outlet. Vertical herein means that the tubular member's length is essentially parallel with the gravitational field vector of the earth (i.e., would be essentially parallel with the plumb line of a plumb bob when determining vertical).

A second aspect of the invention is a reactor comprised of a bottom inlet and a top outlet having vertical tubular member disposed there between, wherein the bottom inlet has separate gas reactant inlet and separate liquid reactant inlet whereby the gas reactant is mixed with the liquid reactant and the outlet has an extraction port, the extraction port extending sufficiently to withdraw the liquid product from the reactor and maintain a gaseous head space within the tubular member of the reactor.

The method and reactor are particularly suited for reacting a liquid reactant and gas reactant that do not react quickly and typically require a catalyst such as the carbonylation of an epoxide by carbon monoxide. Other reactions may include, for example, hydrogenation reactions (e.g., $H_2$ reacted with unsaturated hydrocarbons and hydrocarbon oxidation (e.g., oxygen "air" with cyclohexane).

BRIEF DESCRIPTION OF THE DRAWINGS

FIG. 1 is an illustration of the hybrid vertical tube reactor of this invention.

DETAILED DESCRIPTION

The explanations and illustrations presented herein are intended to acquaint others skilled in the art with the invention, its principles, and its practical application. The specific embodiments of the present disclosure as set forth are not intended to be exhaustive or limit the scope of the disclosure.

The method employs a hybrid vertical bubble plug flow reactor (reactor) 10 illustrated in FIG. 1, but not limited thereto. The reactor 10 has a bottom inlet 20 and top outlet 30 connected by tubular member 40. The bottom inlet is comprised of separate gas reactant inlet 60 and liquid reactant inlet 70. The bottom inlet may be further comprised of a drain 80 or other inlet for introduction of other components. In the bottom inlet 20 the gas reactant is mixed with the liquid reactant which may be mixed with a solvent in mixing area 90. The gas reactant inlet 60 may also be comprised of a sparger (not shown) to cause the formation of desired gas reactant bubble size within the liquid reactant and to facilitate the saturation of the liquid reactant and, if used, solvent. The inlet may further be comprised of a screen mesh or the like 100 or the like to retain optional packing 45 in the vertical tubular member 40 or to further disperse or reduce the gas reactant bubbles. The mesh may be any to be used to encourage the rupture of bubbles into smaller bubbles and retain packing such as the product offered from Sealing Devices Inc., a pipe flange gasket with inlaid 316SS #20 mesh. It is understood that the bottom inlet may be configured in any manner that allows for the injection and mixture of the reactants at the bottom of the tubular member 40 such as radial inlets at the bottom of the tubular member 40 or vertical tubes traversing within the tubular member from the top and exiting at the bottom of tubular member 40.

The outlet 30 is fitted with any suitable gas liquid separation method such as those known in the art. In one embodiment, the outlet 30 is comprised of extraction tube 75 that extends sufficiently into the liquid product, solvent and residual liquid reactant (reactor liquid 50) to allow for the extraction of said reactor liquid 50 and to allow head space 65 to be maintained providing an overpressure of the gas reactant. In an alternative, the extraction tube may be replaced by any other outlet such as a radial extraction port that also allows the headspace to be maintained. The extraction tube, port or other outlet for the liquid product and residual solvent and unreacted liquid reactants, may be accompanied by a separate gas outlet. The outlet 30 has effluent outlet 95 for transporting the reactor liquid 50 for further processing such as separation, further reaction, recovery of solvent and/or catalyst and gaseous outlet 85 for maintaining the overpressure of gases within the reactor utilizing suitable flow controllers, tanks, valves and apparatus such as those known in the art (not pictured), which may be integrated or integral with the reactor.

It has been discovered that the reactor surprisingly may be used to react a gas and liquid reactant. In particular, the method allows for the catalyst to be more effectively and efficiently used realizing high TONs. Turnover Number (TON) is used as commonly understood in the art, wherein for continuous reactions the amount of catalyst and product produced in a given time results in the TON for continuous reactions and is given by (moles product/time)/(moles catalyst/time). TONs indicate the efficacy of the catalyst for continuous reactions where the output of the product is similar. In performing the method of the invention, a liquid reactant is injected into the mixing area 90 through the liquid reactant inlet 70 and the gas reactant is injected into the mixing area 90 through the gas reactant inlet 60 where bubbles of the gas reactant are formed in the liquid reactant. The reactants may be cooled or heated when injected depending on the type of reaction being performed. For example, it may be desirable to inject cooled reactants for exothermic reactions such as carbonylation described herein.

The tubular member 40 is vertically oriented with it being understood some deviation from vertical may be acceptable, but, in essence, the reaction zone is straight without any bends or other obstructions that can entrap the gas reactant. The tubular member 40 may have any cross-sectional shape such a square, rectangle, quadrilateral, hexagon, pentagon oval or circle with a circle being preferred. The materials of construction may be any that is compatible with the reactants and conditions used to react the reactants and is readily determinable by one of ordinary skill in the art. For example, when the reactants are an epoxide and carbon monoxide, stainless steel (e.g., 302 or 316 stainless steel), inorganic glasses, organic plastics (e.g. engineering polymers) and ceramics may be used.

The length of the reactor 10 and tubular member 40 may be any length and diameter useful to realize the desired reaction conditions such as residence time. Typically, the diameter of the tubular member may be from 2 mm, 3 mm, 5 mm or 1 cm to 200 cm, 100 cm, 50 cm, 20 cm or 10 cm. It is understood that the diameter of a non-cylindrical tubular member is taken as the largest dimension of the cross-section of such tubular member. Generally, the aspect ratio (length/diameter) is at least about 10, 15 or 20 to any commercially practicable ratio such as 1000, 500, 200, 100, 75 or 50.

In an embodiment, the reactor 10 may be comprised of multiple tubular members 40 in parallel with separate or shared flanging for injection of the reactants and removal of the products. Such parallel configurations of tubular members 40 may be contained in a common vessel, for example, that may have a heating element or heat transfer fluid to heat or cool such tubular members 40 commonly. In another embodiment, the reactors 10 may be configured in series, for example, to inject further or different reactants or catalysts or react the products from one reactor in a subsequent reactor to form a different product. Likewise, a combination of parallel and series reactors may be configured to allow for the continuous formation of differing products and adjust the mix of such product.

In another embodiment, the tubular member 40 may be further comprised of one or more radial inlets along its length for injecting further reactants or other components (e.g., solvent, stabilizers, surfactants or the like). It is understood that such other components, just like the solvent may also be injected in the bottom inlet. For example, a radial inlet may be used to inject the same gas reactant or liquid reactant inserted in the bottom inlet 20 along the length of the tubular member 40. If a gas reactant is injected through a radial inlet it may incorporate a sparger as described herein. In another embodiment, differing reactants may be inserted through the radial inlet or inlets to form differing desired final products. As previously described, the reactants or any further components may be heated or cooled depending on the desired reaction or reaction conditions.

The rate of injection of the gas reactant/liquid reactant is such that it results in a molar excess of the stoichiometric amount for the desired reaction of the gas reactant. Illustratively, the molar ratio (or equivalent ratio) of the gas reactant/liquid reactant is greater than 1, 1.1. 1.2, 1.4 or 1.5 to about 20, 10, 7, 5, 4 or 3. It is believed, without being limiting in any way, that the excess of gas reactant allows for maintaining of the saturation of the liquid reactant with the gas reactant throughout the resident time within the reactor so as to avoid starvation of the gas reactant in the reactor. Likewise, excess amounts of gas reactant, is believed, without being limiting may cause evaporation of the liquid reactant, product or solvent into the bubbles formed within the liquid reactant and thus inhibiting the catalyzed reaction.

Desirably, the bubbles that are formed in the liquid reactant are of a size that enhances the saturation within the liquid reactant and even distribution throughout the reactor. In an embodiment a sparger may be used when injecting the gas reactant. The sparger may be any commonly used in the chemical or biochemical industries. For example, the sparger may be a porous sintered ceramic frit or porous metal frit such as those available from Mott Corp. Farmington, CT. The pore size of the porous sintered frit sparger may be any useful such as those having a pore size of 0.5 micrometer, 1 micrometer, 2 micrometers to 100 micrometer, 50 micrometers, 20 micrometers or 15 micrometers. Examples of other gas spargers that may be suitable include perforated plate, needle, spider, or combination thereof of varying sized openings depending on the desired gas bubble size.

In another embodiment, the bubble size desired or distribution of the reactants may be facilitated by using packing 45 within the reactor. The packing 45 may be any useful for causing disruption of larger bubble formation and to break up larger bubbles such as those known in the art or distributing of the reactants. For example, the packing 45 may be a porous packing such as commonly used in plug flow reactors to ensure good radial mixing and facilitate plug flow through the reactor. Packing 45 may be beads of any useful shape, a monolithic or segmented inline static mixing structure or screw structure, distribution plates or sieves.

In a further embodiment, the bubble size desired may be facilitated by the use of a surface active agent including but not limited to ionic (cationic, anionic, and amphoteric surfactants) or nonionic surfactants that are separately added. The surface active agent may be entrained in the liquid reactant when inserted or be separately inserted into the inlet 20. In an embodiment, the surface active agent may be insitu produced as a by-product. For example, a glycolic oligomer may be produced when carbonylating an epoxide or lactone with carbon monoxide.

When the packing 45 is a bead, the bead may be any useful shape, such as sphere, spheroid, cone, cylinder, flat perforated sheet having any cross-sectional shape, tube, cube or fibrous. In an embodiment, the beads may be monosized (same volume or equivalent spherical diameter, if not spheres) or of varying sizes including bimodal, trimodal or of a continuous size distribution. Generally, the bead size is 1 mm to about 25.

The size of the beads may be any useful size, that facilitates the plug flow and disruption of the bubble as described above. The packing 45 generally creates a void fraction of about 20% to 99% within the tubular member 40. Typically, the void fraction is 25% or 30% to 80%, 90% or 95%.

The packing 45 may be made of any suitable material useful to handle the reactants and reaction conditions employed. Suitable bead materials may include, for example, ceramics (e.g., crystalline oxides, nitrides, carbides, and amorphous silicates, aluminates, borates and combinations thereof), plastics (e.g., polyolefins, fluoropolymers, polycarbonates, polyesters and combinations thereof), metals (e.g., transition metals and alloys thereof) or combinations of any of the aforementioned. Particular examples include porous, borosilicate glass, silica glass, soda-lime glass, alumina, stainless steel, nickel alloy or combinations thereof. In a particular embodiment, the packing 45 is a perforated 316 stainless steel tabs available under the tradename PRO-PAK (Cannon Instrument Co.). In an embodiment, the method employs both a sparger and packing. In further embodiments, the packing 45 may be catalytic as described below.

In the method, it is desirable for the gas bubbles to flow through the reactor 10 at a velocity (speed) that is the same or faster than the liquid reactant. Without being limiting in any way, this is believed to facilitate the saturation of the gas reactant into the liquid reactant as well as create agitation throughout the reactor improving the reaction efficiency and effectiveness (e.g., higher TONs and selectivity). Typically, the bubbles have a velocity that is at least about 1.1 or 1.5 to 10, 5 or 4 times faster through the reactor 10 than the liquid reactant and any solvent if used. In other words, the bubbles have a residence time that is less than the liquid reactants by a similar proportion as given for the speed (e.g., 0.9 or 0.67 to 0.1, 0.2 or 0.25 the residence time).

In an embodiment, a head space 65 of gas is maintained within tubular member 40, for example, to facilitate the saturation of the gas reactant in the liquid reactant and solvent if used. The head space 65 may be maintained, as previously described, at any pressure useful for reaction conditions used to react particular reactants. As an illustration, when the liquid reactant is an epoxide (e.g., ethylene oxide and/or propylene oxide) or beta lactone (beta butyrolactone and/or beta propiolactone) and gas reactant is carbon monoxide, the pressure may range from greater than 1, 2, 3, 4 or 5 bar to about 100, 50, 20 or 15 bar. In an embodiment, the head space 65 may also be used to facilitate the maintenance of the liquid reactant in the liquid state. For example, if the reactant is normally a gas at ambient conditions (ambient conditions in essence 20 to 25° C. and 1 atm), the liquid reactant may be maintained in part by having a sufficient overpressure such as described above.

The method may be carried out at any useful temperature for the particular reactants and desired product. Illustratively, for the carbonylation of an epoxide or lactone, the temperature may be from about 50° C., 60° C., 70° C. to 200° C., 150° C., 125° C., or 100° C. The heating or cooling of the reactor may be carried out by any suitable method or apparatus such as those known in the art. For example, the reactor 10 may include a temperature controlling jacket, not pictured. Typically, this may involve heat exchanging conduits such as channels in the wall of the tubular member 40, that allows for cooling or heating liquid to pass through and transfer heat into or out of the reactor or it may be any known heating or cooling methods such as heating tape or tube or tubes wrapped around the tubular member 40, channels within the walls of the tubular member 40, or tubes within the tubular member 40 (i.e., the reactants contact the tube walls within the reactor) or any combination thereof to control the temperature of the reaction or immersed heating/cooling tubes within tubular member 40.

The method may use any rate of introduction of the reactants to realize a suitable residence time within the reactor 10. Typically, the residence time within the reactor 10 may be from 2, 5 or 10 minutes to 24 hours, 10 hours, 5 hours, 3 hours, 2 or 1 hour depending on the reactants such as epoxides, lactones or combination thereof with carbon monoxide. In an embodiment, surprisingly, the reactor 10 may be used to carbonylate an epoxide to a lactone, which then further reacts to form an anhydride. It is surprising, because there is a continuous feed of epoxide into the reactor and the catalyst is highly selective in forming the lactone in the presence of the epoxide. The method may also recycle the effluent, for example, to realize a desired product mix and in particular recycled CO, when performing the carbonylation reaction described here may be particularly desirable.

In the method the reaction is carried out in the presence of a catalyst. The catalyst may be a homogeneous catalyst, heterogeneous catalyst or combination thereof. In an embodiment, the catalyst is present in the liquid reactant when injected into the reactor 10 via liquid reactant inlet 70. For example, the catalyst is a homogeneous catalyst dissolved in the liquid reactant or heterogeneous catalyst present as a particle in the liquid reactant (slurry) prior to insertion into the reactor 10. In another embodiment the catalyst is comprised of a heterogenous catalyst that is anchored to a support, which may be use as the packing 45 in part or wholly. As an illustration, the heterogeneous catalyst may be supported catalyst useful in the carbonylation of epoxides or lactones such as described in copending application PCT/US2020/044013 incorporated herein by reference. The support may be a porous ceramic such as a packing bead described above and, in an embodiment, may be a zeolite such as described in paragraph 36 of said copending application incorporated herein by reference, silica, titania, silver (e.g., silver in clay binder). Other exemplary catalysts for carbonylation of epoxides or lactones are described in U.S. Pat. Nos. 6,852,865 and 9,327,280 and U.S. Pat. Appl. Nos. 2005/0014977 and 2007/0213524 each incorporated herein by reference.

The amount of catalyst may be any useful amount and may depend on the particular reactants and desired product. Typically, the amount of catalyst present in the reactor is about 0.001% to 20% by weight of the amount of reactants present in the reactor 10. Illustratively, if the catalyst is a homogeneous catalyst dissolved or entrained in the liquid reactant, the amount of the catalyst is about 0.001%, 0.01%, 0.05% to about 20%, 10% or 5% by weight of the liquid reactant and catalyst. As a further illustration, the amount of homogeneous catalyst when carbonylating an epoxide or lactone with carbon monoxide is fed into the reactor along with the epoxide or lactone at molar ratio of liquid reactant/catalyst of 50, 100 to 50,000, 25,000, 10,000, 5,000 or 2,500.

The liquid reactant may be present, mixed with or entrained in a solvent. Any useful solvent may be used. The solvent may be used to enhance, for example, the presence of the gas reactant in the liquid reactant. As an illustration, when the liquid reactant is an epoxide, the solvent may be an organic solvent such as an aliphatic hydrocarbon, aromatic hydrocarbon, halogenated solvent, ether, ester, ketone, nitrile, amide, carbonate, alcohol, amine, sulfone, mixture thereof or combination thereof. Exemplary solvents may include diethyl ether, methy-t-butyl ether, tetrahydrofuran, 1,4-dioxane, glyme, diglyme, triglyme, higher glymes, or mixtures thereof. The amount of solvent may be any useful amount for performing the method and may vary over a wide range. For example, the amount of solvent to liquid reactant by weight (solvent/liquid reactant) may vary from 1, 10 or 20 to 99, 90, or 80.

The gas reactant may also be present, mixed with or entrained in another gas. The gas reactant for example may be mixed with another gas such as an inert gas or nitrogen. In a particular embodiment, the reactant gas is carbon monoxide that is mixed with hydrogen such as in a commercial syngas, which may be used in the carbonylation of an epoxide, lactone or combination thereof as described in U.S. Pat. No. 10,597,294, incorporated herein by reference.

In a particular embodiment of the method, the liquid reactant is an epoxide or lactone and carbon monoxide to form their corresponding carbonylation lactone, anhydride products. refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted. In some embodiments, epoxides comprise a single oxirane moiety. In some embodiments, epoxides comprise two or more oxirane moieties. Lactone may be any lactone such as those produced when carbonylating the aforementioned epoxides. Examples of such epoxides and lactones include ethylene oxide, propylene oxide and their corresponding lactone carbonylation products beta propiolactone and beta butyrolactone. Examples of such lactones include beta propiolactone and beta butyrolactone and their corresponding carbonylation products succinic anhydride and methylsuccinic anhydride. Further examples of epoxides and lactones are in Table A (between paragraphs 65 and 66) of PCT Pub. WO2020/033267 incorporated herein by reference.

ILLUSTRATIVE EMBODIMENTS

The following examples are provided to illustrate the method and reactor without limiting the scope of the invention. All parts and percentages are by weight unless otherwise noted. Table 1 shows the ingredients used in the Examples and Comparative Examples.

Examples

A lab scale hybrid bubble plug flow reactor 10 made of 316 stainless steel and tubular member 40 fabricated using a 1 inch diameter pipe that is 2 feet long having flanges at the top outlet 20 and bottom outlet 30 in a similar manner as depicted in FIG. 1, except that the gas reactant inlet and liquid reactant inlet and drain were made using a two radial port bleed flange and a bottom drain valve 80. The tubular member 40 is packed with PROPAK packing leaving about 1 inch head space 65. The reactor has a 316 stainless strainer 100 (a pipe flange gasket with inlaid 316SS #20 mesh available from Sealing Devices Inc) at the top of the bottom bleeder flange. A ¼" 316 stainless steel dip tube 75 is used to extract the effluent as described herein.

The reactor is preheated and maintained at the temperature shown in Table 1. Ethylene oxide in tetrahydrofuran (THF) is injected into the reactor and CO is separately injected into the reactor as shown in Table 1 for each Example. Each Example is run over a period of hours ensuring that the reaction occurs over multiple residence times. The catalyst used is the same for each example. The catalyst is essentially the same as described in US Pub. No. 2019-0030520. The effluent composition and concentrations are shown in Table 2. The performance metrics of the reactor are shown in Table 3. All concentrations are by mass unless indicated otherwise. No gas bubble accumulation is observed in any of the Examples.

Example 1 shows that an anhydride may be made in the reactor in one reactor. The other Examples display the wide variety of run conditions that may be used when reacting a liquid and gas reactant.

Example 17 is made using the same reactor as Examples 1-16 and run under the conditions shown in Table 4. Comparative example 1 is made in a continuously stirred reactor under conditions having a substantially comparable residence time and reactor outlet beta propiolactone (bPL) concentration as Example 17, which is also shown in Table 4. From this, it is readily apparent that the reactor of the present invention has a much higher TON for a given residence time and bPL output than a continuously stirred reactor operating under similar conditions and product output. Surprisingly, the bPl output is equivalent using substantially less catalyst per mole of product produce and essentially the same residence time, which is reflected in the substantial increase in the TON on a unit time basis.

TABLE 1

| | | | | | Run Conditions | | | | | | | |
|---|---|---|---|---|---|---|---|---|---|---|---|---|
| Date | CO Rate (g/min) | CO/EO molar ratio | T [C.] | P [PSIg] | Reactor Mass [g] | THF Rate [g/min] | EO Rate [g/min] | Catalyst Soln Rate [g/min] | Catalyst Conc. [mM] | Calculated Res Time [min] | EO/ THF feed ratio | Cat Conc. In rxr [M] |
| Ex. 1 | 6.7 | 11.3 | 80 | 950 | 235 | 5.639559 | 0.927712 | 0.432727 | 35 | 30 | 0.164501 | 2.16E−06 |
| Ex. 2 | 6.7 | 10.8 | 70 | 950 | 235 | 5.68 | 0.97 | 0.38 | 1 | 30 | 0.170775 | 5.41E−08 |

TABLE 1-continued

| | | Run Conditions | | | | | | | | | | |
|---|---|---|---|---|---|---|---|---|---|---|---|---|
| Date | CO Rate (g/min) | CO/EO molar ratio | T [C.] | P [PSIg] | Reactor Mass [g] | THF Rate [g/min] | EO Rate [g/min] | Catalyst Soln Rate [g/min] | Catalyst Conc. [mM] | Calculated Res Time [min] | EO/THF feed ratio | Cat Conc. In rxr [M] |
| Ex. 3 | 6.7 | 10.8 | 80 | 950 | 235 | 5.68 | 0.97 | 0.38 | 1 | 30 | 0.170775 | 5.41E−08 |
| Ex. 4 | 6.7 | 20.3 | 80 | 950 | 235 | 3.182899 | 0.51913 | 0.214567 | 1 | 54 | 0.1631 | 5.48E−08 |
| Ex. 5 | 6.7 | 20.3 | 100 | 950 | 235 | 3.182899 | 0.51913 | 0.214567 | 1 | 54 | 0.1631 | 5.48E−08 |
| Ex. 6 | 6.7 | 10.1 | 80 | 950 | 235 | 6.624903 | 1.038468 | 0.169998 | 5 | 27 | 0.156752 | 1.09E−07 |
| Ex. 7 | 3.6 | 11.3 | 100 | 950 | 235 | 6.5 | 0.5 | 0.16 | 5 | 30 | 0.076923 | 1.12E−07 |
| Ex. 8 | 3.6 | 11.3 | 110 | 950 | 235 | 6.5 | 0.5 | 0.1 | 5 | 30 | 0.076923 | 7.04E−08 |
| Ex. 9 | 3.6 | 9.4 | 100 | 950 | 235 | 3 | 0.6 | 0.4 | 1 | 53 | 0.2 | 0.0000001 |
| Ex. 10 | 3.6 | 18.9 | 100 | 950 | 235 | 6.5 | 0.3 | 0.5 | 1 | 29 | 0.046154 | 6.85E−08 |
| Ex. 11 | 3.6 | 37.7 | 100 | 950 | 235 | 3.25 | 0.15 | 0.25 | 1 | 58 | 0.046154 | 6.85E−08 |
| Ex. 12 | 3.6 | 41.1 | 100 | 950 | 235 | 2.08 | 0.1375 | 0.07557 | 1 | 92 | 0.066106 | 3.30E−08 |
| Ex. 13 | 1.6 | 4.2 | 100 | 950 | 235 | 3 | 0.6 | 0.6 | 1 | 50 | 0.2 | 1.43E−07 |
| Ex. 14 | 1.6 | 8.4 | 100 | 950 | 235 | 6.5 | 0.3 | 0.6 | 1 | 29 | 0.046154 | 8.11E−08 |
| Ex. 15 | 1.6 | 8.4 | 100 | 950 | 235 | 3 | 0.3 | 0.6 | 1 | 54 | 0.1 | 1.54E−07 |
| Ex. 16 | 1.6 | 10.1 | 100 | 950 | 235 | 2.9 | 0.25 | 0.18 | 5 | 64 | 0.086207 | 2.70E−07 |

M = Molarity [mol/L]
THF = Tetrahydrofuran
EO = Ethylene Oxide

TABLE 2

| | Effluent Concentrations | | | | |
|---|---|---|---|---|---|
| | ACH | EO | bPL | SAH | THF |
| Ex. 1 | 3.30% | 0.00% | 4.30% | 9.20% | 83.20% |
| Ex. 2 | 0.00% | 6.40% | 0.48% | 0.00% | 93.12% |
| Ex. 3 | 0.00% | 5.50% | 0.76% | 0.00% | 93.74% |
| Ex. 4 | 0.00% | 6.20% | 1.64% | 0.00% | 92.16% |
| Ex. 5 | 0.08% | 2.00% | 7.35% | 0.00% | 90.57% |
| Ex. 6 | 0.00% | 5.20% | 1.00% | 0.00% | 93.80% |
| Ex. 7 | 0.25% | 3.60% | 4.30% | 0.00% | 91.85% |
| Ex. 8 | 0.50% | 3.65% | 3.84% | 0.00% | 92.01% |
| Ex. 9 | 0.60% | 6.60% | 9.80% | 0.00% | 83.00% |
| Ex. 10 | 0.22% | 3.27% | 2.99% | 0.00% | 93.52% |
| Ex. 11 | 0.35% | 1.92% | 5.42% | 0.00% | 92.31% |
| Ex. 12 | 0.20% | 3.00% | 3.60% | 0.00% | 93.20% |
| Ex. 13 | 0.39% | 7.50% | 7.20% | 0.00% | 84.91% |
| Ex. 14 | 0.11% | 6.30% | 2.10% | 0.00% | 91.49% |
| Ex. 15 | 0.47% | 3.60% | 8.20% | 0.00% | 87.73% |
| Ex. 16 | 0.66% | 2.90% | 11.50% | 0.00% | 84.94% |

ACH = Acetalaldehyde byproduct.
EO = Ethylene Oxide
bPL = Beta propiolactone
SAH = Succinic anhydride
THF = Tetrahydrofuran

TABLE 3

| | TON [mol bpl/min]/[mol cat/min] | TON/res time (min) | Productivity [mol bPL/min/L] |
|---|---|---|---|
| Ex. 1 | 240.5571383 | 7.9616997 | 0.01722622 |
| Ex. 2 | 963.1036354 | 32.012381 | 0.0017304 |
| Ex. 3 | 1514.828248 | 50.351029 | 0.00272168 |
| Ex. 4 | 3299.676195 | 61.104012 | 0.00334753 |
| Ex. 5 | 15047.79663 | 278.65787 | 0.01526601 |
| Ex. 6 | 1038.658745 | 38.469018 | 0.00417423 |
| Ex. 7 | 4754.695155 | 160.96273 | 0.01798466 |
| Ex. 8 | 6781.871536 | 227.66566 | 0.01603279 |
| Ex. 9 | 11069.27711 | 209.34803 | 0.0209348 |
| Ex. 10 | 5195.412746 | 179.32157 | 0.0122823 |
| Ex. 11 | 9541.219803 | 164.65935 | 0.01127804 |
| Ex. 12 | 13289.5573 | 144.08456 | 0.00474843 |
| Ex. 13 | 5299.729125 | 105.24285 | 0.01503469 |
| Ex. 14 | 3108.263198 | 108.75247 | 0.00881777 |
| Ex. 15 | 5841.787302 | 107.7209 | 0.01657245 |
| Ex. 16 | 5453.19572 | 85.858826 | 0.02320509 |

TON = Turnover number

TABLE 4

| Example | Inputs | | | | | | Catalyst Solution Rate [g/min] | Catalyst Solution Concentration [mM] | Output | |
|---|---|---|---|---|---|---|---|---|---|---|
| | Temperature [C.] | Pressure [psi] | Residence Time [min] | THF rate [g/min] | EO rate [g/min] | | | | bPL wt % | TON [(mol bPL/min)/ (mol catalyst/min)] |
| Comp. Ex. 1 | 100 | 1100 | 60 | 10.5 | 0.9 | | 0.24 | 5 | 5.30% | 6500 |
| Ex. 17 | 100 | 1100 | 53 | 3.2 | 0.52 | | 0.25 | 1 | 5.30% | 10000 |

What is claimed is:

1. A method of reacting a gas reactant and liquid reactant comprising;
   (i) introducing the gas reactant and liquid reactant into a hybrid vertical bubble plug flow reactor, having a bottom inlet and a top outlet connected by a tubular member, separately at the bottom inlet, wherein the gas reactant and liquid reactant are mixed and introduced at a rate resulting in a molar ratio of gas reactant/liquid reactant that is in excess of a stoichiometric amount and the gas reactant forms bubbles within the liquid reactant, wherein the liquid reactant is a gas at ambient conditions and the reactor is maintained at a pressure and temperature for the liquid reactant to be maintained as a liquid and the bubbles traverse the reactor at a speed and the liquid reactant traverse the reactor at a speed and the speed of the bubbles is the same or greater than the speed of the liquid reactant,
   (ii) allowing the gas and liquid reactants to react and form a reaction product as they flow upwards through the hybrid vertical bubble plug flow reactor in the presence of a catalyst, and
   (iii) removing the reaction product at the top outlet.

2. The method of claim 1, wherein a gaseous head space is maintained in the reactor.

3. The method of claim 1, wherein the molar ratio of gas reactant/liquid reactant is from 1.2 to about 20.

4. The method of claim 1, wherein the tubular member of the reactor has packing therein, and the gas reactant is introduced through a sparger.

5. The method of claim 1, wherein the liquid reactant is dissolved within a solvent.

6. The method of claim 1, wherein the speed of the bubbles is at least 1.1 to 10 times faster than the speed of the liquid.

7. The method of claim 1, wherein the gas reactant is carbon monoxide and the liquid reactant is an epoxide or a beta lactone.

8. The method of claim 1, wherein the catalyst is comprised of a homogeneous catalyst that is introduced with the reactants and flows through the reactor with the reactants and reaction products.

9. The method of claim 8, wherein the homogeneous catalyst is mixed with the liquid reactant and introduced with the liquid reactant into the reactor.

10. The method of claim 1, wherein the catalyst is comprised of a heterogeneous catalyst affixed to a support that is distributed within the tubular member of the reactor.

11. The method of claim 1, wherein the pressure is maintained from about 1 bar to about 100 bars.

12. The method of claim 1, wherein more than one reactor is employed in series, parallel or combination thereof.

13. The method of claim 12, wherein there is at least two reactors in series and the product of one reactor is the liquid reactant in a subsequent reactor.

14. The method of claim 1, wherein the reactor has an aspect ratio of length/diameter of at least about 10.

15. The method of claim 1 wherein the temperature is about 50° C. to 200° C.

16. The method of claim 1 where a surface active agent is present in the reactor.

17. The method of claim 16, wherein the surface active agent is generated insitu during the reaction as a byproduct.

18. The method of claim 1, wherein the bubbles are of a size that maintains the saturation of the gas reactant within the liquid reactant and, if present, any solvent.

19. The method of claim 1 further comprising injecting the gas reactant, liquid reactant, other reagent, or combination thereof along the length of the tubular member of the hybrid vertical bubble plug flow reactor.

20. The method of claim 1 wherein the liquid reactant is comprised of an epoxide and the gas reactant is comprised of carbon monoxide, the reaction product is comprised of an anhydride and said method is performed in one hybrid vertical bubble plug flow reactor.

* * * * *